US005635363A

United States Patent [19]
Altman et al.

[11] Patent Number: 5,635,363
[45] Date of Patent: Jun. 3, 1997

[54] COMPOSITIONS AND METHODS FOR THE DETECTION, QUANTITATION AND PURIFICATION OF ANTIGEN-SPECIFIC T CELLS

[75] Inventors: John D. Altman, San Carlos; Michael G. McHeyzer-Williams, Menlo Park; Mark M. Davis, Atherton, all of Calif.

[73] Assignee: The Board of Trustees of the Leland Stanford Junior University, Stanford, Calif.

[21] Appl. No.: 396,220

[22] Filed: Feb. 28, 1995

[51] Int. Cl.$^6$ ............... C07K 14/74; G01N 33/566
[52] U.S. Cl. ............... 435/7.24; 435/7.5; 435/2; 530/395; 530/868
[58] Field of Search ............... 435/7.24, 240.2, 435/7.5; 530/395, 868

[56] References Cited

U.S. PATENT DOCUMENTS

| | | | |
|---|---|---|---|
| 4,400,376 | 8/1983 | Sanderson | 424/88 |
| 4,478,823 | 10/1984 | Sanderson | 424/88 |
| 5,194,253 | 3/1993 | Sharma et al. | 514/8 |
| 5,468,481 | 11/1995 | Sharma et al. | 424/125.1 |

OTHER PUBLICATIONS

Bjorkman, et al., Structure of the Human Class I Histocompatibility Antigen, HLA-A-A2 (Oct. 1987) Nature, vol. 329, pp. 506–512.

Schatz, Use of Peptide Libraries to Map the Substrate Specificity of a Peptide-Modifying Enzyme: A 13 Residue Consensus Peptide Specifies Biotinylation in *Escherichia coli*(11 Oct. 1993) Bio/Technology, vol. 11, pp. 1138–1143.

Brown, et al., Three-Dimensional Structure of the Human Class II Histocompatibility Antigen HLA-DR1 ( 1 Jul. 1993) Nature, vol. 364, pp. 33–39.

Matsui, et al., Low Affinity Interaction of Peptide-MHC Complexes with T Cell Receptors (20 Dec. 1991) Science, vol. 254, pp. 1788–1791.

Garboczi, et al., HLA-A2-Peptide Complexes: Refolding and Crystallization of Molecules Expressed in *Escherichia coli*and Complexed with Single Antigenic Peptides (Apr. 1992) Proc. Natl. Acad. Sci. USA 89, pp. 3429–3433.

Altman, et al., Formation of Functional Peptide Complexes of Class II Major Histocompatability Complex Proteins from Subunits Produced in *Escherichia coli*(Nov. 1993) Proc. Natl. Acad. Sci. USA, vol. 90, pp. 10330–10334.

Fridkis-Hareli, et al., Direct Binding of Myelin Basic Protein and Synthetic Copolymer 1 to Class II Major Histocompatibility Complex Molecules on Living Antigen-Presenting Cells—Specificity and Promiscuity (May 1994) Proc. Natl. Acad. Sci. USA, vol. 91, pp. 4872–4876.

Tompkins, et al., A Europium Fluoroimmunoassay for Measuring Binding of Antigen to Class II MHC Glycoproteins (1993) Jour. of Immuno. Methods, 163, pp. 209–216.

Romero, et al., Photoaffinity Labeling of the T Cell Receptor on Living Cytotoxic T Lymphocytes (May 1, 1993) The Jour. of Immuno., vol. 150, 3825–3831, No. 9.

Invention Disclosure: Altman, et al., Detection, Enumeration and Purification of Antigen-Specific T Cells (Dec. 29, 1993) Stanford University, Stanford, CA.

L. E. Hood et al *Immunology*, Second Edition, The Benjamin/Cummings Publishing Company, Inc., 1984, pp. 66–67.

W. C. A. Van Schooten et al, Jour. Immunol., 148, 1043–1048, 1992.

Parish et al., "Detection of a Glycosylation-Dependent Ligand for the T Lymphocyte Cell Adhesion Molecule CD2 Using a Novel Multimeric Recombinant CD2-Binding Assay," J. of Immunology (Jun. 1993), 150:4833–4843.

*Primary Examiner*—David Saunders
*Attorney, Agent, or Firm*—Pamela J. Sherwood; Fish & Richardson P.C.

[57] ABSTRACT

T cells are specifically labeled according to their antigen receptor by binding of a multimeric binding complex. The complex is prepared with major histocompatibility complex protein subunits having a homogeneous population of peptides bound in the antigen presentation site. The multimeric MHC-antigen complex forms a stable structure with T cells, thereby allowing for the labeling, identification and separation of specific T cells.

16 Claims, 2 Drawing Sheets

COMPOSITIONS AND METHODS FOR THE DETECTION, QUANTITATION AND PURIFICATION OF ANTIGEN-SPECIFIC T CELLS

This invention was made with Government support under NIH Grant no. AI22511. The Government has certain rights in this invention.

TECHNICAL FIELD

The field of this invention is polymeric antigen compositions which specifically label the antigen receptor of T cells.

BACKGROUND

T lymphocytes compose a major part of the body's immune defenses against bacterial, viral and protozoal infection, and have been implicated in the rejection of cancerous cells. Numerous autoimmune syndromes have also been linked to antigen-specific T cell attack on various parts of the body. It is therefore of great interest to be able to track antigen-specific T cells during the course of these diseases. It would also be of great therapeutic benefit if T cells specific for a particular antigen could be enriched and then reintroduced in a disease situation, or selectively depleted in the case of an autoimmune disorder.

Current technology for isolating or otherwise identifying antigen-specific T cells is very crude. While the T cell antigen receptors (TCR) are structurally and genetically similar to antibodies, their ligands are complex, consisting of a peptide embedded in a molecule of the major histocompatibility complex. MHC proteins come in two basic types, class I and class II, each of which subserves a particular type of T cell. Class I molecules interact with $CD8^+$ T cells, whereas class II molecules interact with $CD4^+$ T cells. The two types of MHC molecules differ in the length of peptide which they are able to present. The class I peptide binding pocket is blocked at either end, thereby imposing severe restrictions on the sizes of peptides it can accommodate (8–10 residues), with longer peptides bulging out in the middle. The class II binding groove allows peptides to protrude from the ends, and consequently much longer peptides, (8–30 residues) can bind.

Production of monoclonal antibody reagents specific for various T cell variable region epitopes has been difficult. Further, labeling cells with these reagents is of limited utility when one is interested in characterizing T cells having a particular antigenic specificity. Monoclonal antibodies are usually directed to the TCR variable region, including relatively conserved sequences, not to the actual TCR binding site. Monoclonal antibodies may detect T cells having the same variable region but different antigenic specificity, while failing to detect T cells with the same antigenic specificity but a different variable region.

Previous attempts to use MHC protein-peptide complexes to label specific T cells have been unsuccessful, primarily due to the short half-life of the peptide-MHC-T cell receptor ternary complex. At room temperature, the half-life of the ternary complex is only 12 to 25 seconds. Because of the crucial role that the T-cell plays as a major component of the immune system, it remains of great importance to be able to understand how T-cells are selected, activated or tolerized. Specific tracking and the ability to physically purify or ablate antigen specific T cells is of particular interest.

Relevant Literature

The molecular structure of a class I major histocompatibility antigen is described in Bjorkman et al. (1987) *Nature* 329:506–512. The structure of a class II MHC antigen is described in J. Brown et al. (1993) *Nature* 364:33–39. The low affinity of the ternary complex formed between T cell receptor, MHC antigen and antigenic peptide is described in K. Matsui et al. (1991) *Science* 254:1788–1791. While affinities of T cell receptors range from $10^{-4}$ to $10^{-7}$M, the t½, which governs the complex stability, is very similar between high and low affinity receptors, ranging from 12 to 25 seconds at room temperature.

Refolding and crystallization of class I MHC—peptide complexes is described in Garboczi et al. (1992) *P.N.A.S.* 89:3429–3433. Formation of functional class II complexes is described in Altman et al. (1993) *P.N.A.S.* 90: 10330–10334.

The substrate specificity of the *E. coli* BirA enzyme is described in P. Schatz (1993) *Bio/Technology* 11:1138–1143.

Various methods for analyzing peptide binding to T cell receptor and to major histocompatibility complex antigens have been explored. Fridkis-Hareli et al. (1994) *P.N.A.S.* 91:4872–4876 discuss the binding of peptides to class It MHC molecules on living cells. A europium fluoroimmunoassay has also been used to measure binding of antigen to class II MHC proteins, Tompkins et al. (1993) *J. Immunol. Meth.* 163:209–216. Photoaffinity labeling of the T cell receptor is discussed in Romero et al. (1993) *J. Immunol.* 150:3825–3831.

SUMMARY OF THE INVENTION

Methods and compositions are provided for labeling T cells according to the specificity of their antigen receptor. A stable multimeric complex is prepared with major histocompatibility complex protein subunits having a substantially homogeneous bound peptide population. The multimeric MHC-antigen complex forms a stable structure with T cells recognizing the complex through their antigen receptor, thereby allowing for the labeling, identification and separation of specific T cells. The subject methods are also useful for the diagnosis and monitoring of diseases having an immune component.

DESCRIPTION OF THE SPECIFIC EMBODIMENTS

Compositions are provided that label T cells according to the specificity of their antigen receptor. A stable multimeric complex of MHC protein subunits and peptide antigen is prepared. The specificity of the multimeric binding complex is determined both by the antigenic peptide and the MHC protein. The binding complex binds stably with the antigen receptor on the surface of T cells, allowing the detection of antigen specific T cells. The binding complex is useful for detection, quantitation, characterization and separation of specific T cells. Variants of the binding complex for different MHC proteins and peptide antigens are easily produced.

The T cell receptor (TCR) specificity determines what antigens will activate that particular T cell. Usually T helper cells express CD4 on their surface, and are activated by binding to a complex of antigenic peptide and Class II MHC molecule. Usually cytolytic T cells express CD8 on their surface, and are activated by binding to a complex of antigenic peptide and Class I MHC molecule. The specificity of the T cell antigen receptor is the combination of peptide and MHC molecule that binds to that particular TCR with sufficient affinity to activate the T cell. The binding affinity will usually be at least about $10^{-4}$M, as described in Matsui et al., supra.

The binding complex may have a wide variety of peptide-MHC combinations. Multimers of class I MHC molecules will usually be used to detect $CD8^+$ T cells, and class II multimers will usually be used to detect $CD4^+$ T cells. Quantitation of T cells may be performed to monitor the progression of a number of conditions associated with T cell activation, including autoimmune diseases, graft rejection, vital infection, bacterial and protozoan infection. T cells having a particular antigenic specificity may be separated from complex mixtures, particularly biological samples, through binding to the binding complexes. In this way selective depletion or enrichment of particular T cells can be made.

The multimeric binding complex has the formula $(\alpha\text{-}\beta\text{-}P)_n$, where $n \geq 2$, usually $n \geq 4$, and usually $n \leq 10$. $\alpha$ is an $\alpha$ chain of a class I or class II MHC protein. $\beta$ is a $\beta$ chain, herein defined as the $\beta$ chain of a class II MHC protein or $\beta_2$ microglobulin for a MHC class I protein. P is a peptide antigen. The multimeric complex stably binds through non-covalent interactions to a T cell receptor having the appropriate antigenic specificity. When compared to the binding of an $(\alpha\text{-}\beta\text{-}P)$ "monomer" to a T cell, the binding complex will have greatly increased stability, usually having an increase of at least about 10-fold in t½, more usually an increase of about 20-fold, and may be increased as much as about 50-fold.

The MHC proteins may be from any mammalian or avian species, e.g. primate sp., particularly humans; rodents, including mice, rats and hamsters; rabbits; equines, bovines, canines, felines; etc. Of particular interest are the human HLA proteins, and the murine H-2 proteins. Included in the HLA proteins are the class II subunits HLA-DPα, HLA-DPβ, HLA-DQα, HLA-DQβ, HLA-DRα and HLA-DRβ, and the class I proteins HLA-A, HLA-B, HLA-C, and $\beta_2$-microglobulin. Included in the murine H-2 subunits are the class I H-2K, H-2D, H-2L, and the class II I-Aα, I-Aβ, I-Eα and I-Eβ, and $\beta_2$-microglobulin. Sequences of some representative MHC proteins may be found in Kabat et al. *Sequences of Proteins of Immunological Interest*, NIH Publication No. 91-3242, pp724–815.

In a preferred embodiment, the MHC protein subunits are a soluble form of the normally membrane-bound protein. The soluble form is derived from the native form by deletion of the transmembrane domain. Conveniently, the protein is truncated, removing both the cytoplasmic and transmembrane domains. The protein may be truncated by proteolytic cleavage, or by expressing a genetically engineered truncated form. As a reference, the alignment of amino acids into domains shown in Kabat et al., ibid. will be used.

For class I proteins, the soluble form will include the α1, α2 and α3 domain. Not more than about 10, usually not more than about 5, preferably none of the amino acids of the transmembrane domain will be included. The deletion may extend as much as about 10 amino acids into the α3 domain, preferably none of the amino acids of the α3 domain will be deleted. The deletion will be such that it does not interfere with the ability of the α3 domain to fold into a disulfide bonded structure. The class Iβ chain, $\beta_2$-microglobulin, lacks a transmembrane domain in its native form, and need not be truncated. Generally, no Class II subunits will be used in conjunction with Class I subunits.

Soluble class II subunits will include the α1 and α2 domains for the α subunit, and the β1 and β2 domains for the β subunit. Not more than about 10, usually not more than about 5, preferably none of the amino acids of the transmembrane domain will be included. The deletion may extend as much as about 10 amino acids into the α2 or β2 domain, preferably none of the amino acids of the α2 or β2 domain will be deleted. The deletion will be such that it does not interfere with the ability of the α2 or β2 domain to fold into a disulfide bonded structure.

One may wish to introduce a small number of amino acids at the polypeptide termini, usually not more than 20, more usually not more than 15. The deletion or insertion of amino acids will usually be as a result of the needs of the construction, providing for convenient restriction sites, addition of processing signals, ease of manipulation, improvement in levels of expression, or the like. In addition, one may wish to substitute one or more amino acids with a different amino acid for similar reasons, usually not substituting more than about five amino acids in any one domain.

The α and β subunits may be separately produced and allowed to associate in vitro to form a stable heteroduplex complex (see Altman et al. [1993], supra. or Garboczi et al. (1992) supra.), or both of the subunits may be expressed in a single cell. An alternative strategy is to engineer a single molecule having both the α and β subunits. A "single-chain heterodimer" is created by fusing together the two subunits using a short peptide linker, e.g. a 15 to 25 amino acid peptide or linker. See Bedzyk et al. (1990) *J. Biol. Chem.* 265:18615 for similar structures with antibody heterodimers. The soluble heterodimer may also be produced by isolation of a native heterodimer and cleavage with a protease, e.g. papain, to produce a soluble product.

In a preferred embodiment, soluble subunits are independently expressed from a DNA construct encoding a truncated protein. For expression, the DNA sequences are inserted into an appropriate expression vector, where the native transcriptional initiation region may be employed or an exogenous transcriptional initiation region, i.e. a promoter other than the promoter which is associated with the gene in the normally occurring chromosome. The promoter may be introduced by recombinant methods in vitro, or as the result of homologous integration of the sequence into a chromosome. A wide variety of transcriptional initiation regions are known for a wide variety of expression hosts, where the expression hosts may involve prokaryotes or eukaryotes, particularly *E. coli*, *B. subtilis*, mammalian cells, such as CHO cells, COS cells, monkey kidney cells, lymphoid cells, particularly human cell lines, and the like. Generally a selectable marker operative in the expression host will be present.

Of particular interest are expression cassettes comprising a transcription initiation region, the gene encoding the subject MHC subunit, and a transcriptional termination region, optionally having a signal for attachment of a poly A sequence. Suitable restriction sites may be engineered into the termini of the MHC subunit, such that different subunits may be put into the cassette for expression. Restriction sites may be engineered by various means, e.g. introduction during polymerase chain reaction, site directed mutagenesis, etc.

The subunits are expressed in a suitable host cell, and, if necessary, solubilized. The two subunits are combined with an antigenic peptide and allowed to fold in vitro to form a stable heterodimer complex with intrachain disulfide bonded domains. The peptide may be included in the initial folding reaction, or may be added to the empty heterodimer in a later step. Usually the MHC binding site will be free of peptides prior to addition of the target antigenic peptide. The exception will be those cases where it is desirable to label the T cells with a natural peptide-MHC complex, such as those that may be present on the surface of cells that are a target for autoimmune attack, etc.

The MHC heterodimer will bind an antigenic peptide in the groove formed by the two membrane distal domains, either $\alpha 2$ and $\alpha 1$ for class I, or $\alpha 1$ and $\beta 1$ for class II. The bound peptide will be substantially homogenous, that is, there will be less than about 10% of the bound peptides having an amino acid sequence different from the desired sequence, usually less than about 5%, and more usually less than about 1%.

Conditions that permit folding and association of the subunits and peptide are known in the art, see for example Altman et al. (1993) and Garboczi et al. (1992). As one example of permissive conditions, roughly equimolar amounts of solubilized et and $\beta$ subunits are mixed in a solution of urea. Refolding is initiated by dilution or dialysis into a buffered solution without urea. Peptides are loaded into empty class II heterodimers at about pH 5 to 5.5 for about 1 to 3 days, followed by neutralyzation, concentration and buffer exchange. However, it will be readily understood by one of skill in the art that the specific folding conditions are not critical for the practice of the invention.

The antigenic peptide will be from about 6 to 12 amino acids in length for complexes with class I MHC proteins, usually from about 8 to 10 amino acids. The peptide will be from about 6 to 20 amino acids in length for complexes with class II MHC proteins, usually from about 10 to 18 amino acids. The peptides may have a sequence derived from a wide variety of proteins. In many cases it will be desirable to use peptides which act as T cell epitopes. The epitopic sequences from a number of antigens are known in the art. Alternatively, the epitopic sequence may be empirically determined, by isolating and sequencing peptides bound to native MHC proteins, by synthesis of a series of peptides from the target sequence, then assaying for T cell reactivity to the different peptides, or by producing a series of binding complexes with different peptides and quantitating the T cell binding. Preparation of fragments, identifying sequences, and identifying the minimal sequence is amply described in U.S. Pat. No. 5,019,384, iss. May 28, 1991, and references cited therein.

The peptides may be prepared in a variety of ways. Conveniently, they can be synthesized by conventional techniques employing automatic synthesizers, or may be synthesized manually. Alternatively, DNA sequences can be prepared which encode the particular peptide and may be cloned and expressed to provide the desired peptide. In this instance a methionine may be the first amino acid. In addition, peptides may be produced by recombinant methods as a fusion to proteins that are one of a specific binding pair, allowing purification of the fusion protein by means of affinity reagents, followed by proteolytic cleavage, usually at an engineered site to yield the desired peptide (see for example Driscoll et al. (1993) J. Mol. Bio. 232:342–350). The peptides may also be isolated from natural sources and purified by known techniques, including, for example, chromatography on ion exchange materials, separation by size, immunoaffinity chromatography and electrophoresis.

The monomeric complex ($\alpha$-$\beta$-P) (herein monomer) is multimerized. The resulting multimer will be stable over long periods of time. Usually not more than about 10% of the multimer will be dissociated after storage at 4° C. for about one day, more usually after about one week. Preferably, the multimer will be formed by binding the monomers to a multivalent entity through specific attachment sites on the $\alpha$ or $\beta$ subunit, as described below in detail. The multimer may also be formed by chemical cross-linking of the monomers. A number of reagents capable of cross-linking proteins are known in the art, illustrative entities include: azidobenzoyl hydrazide, N-[4-(p-azidosalicylamino)butyl]-3'-[2'-pyridyldithio] propionamide), bis-sulfosuccinimidyl suberate, dimethyladipimidate, disuccinimidyltartrate, N-$\gamma$-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, formaldehyde and succinimidyl 4-[N-maleimidomethyl] cyclohexane-1-carboxylate.

The attachment site for binding to a multivalent entity may be naturally occurring, or may be introduced through genetic engineering. The site will be a specific binding pair member or one that is modified to provide a specific binding pair member, where the complementary pair has a multiplicity of specific binding sites. Binding to the complementary binding member can be a chemical reaction, epitope-receptor binding or hapten-receptor binding where a hapten is linked to the subunit chain. In a preferred embodiment, one of the subunits is fused to an amino acid sequence providing a recognition site for a modifying enzyme. The recognition sequence will usually be fused proximal to the carboxy terminus of one of the subunit to avoid potential hindrance at the antigenic peptide binding site. Conveniently, an expression cassette will include the sequence encoding the recognition site.

Modifying enzymes of interest include BirA, various glycosylases, farnesyl protein transferase, protein kinases and the like. The subunit may be reacted with the modifying enzyme at any convenient time, usually after formation of the monomer. The group introduced by the modifying enzyme, e.g. biotin, sugar, phosphate, farnesyl, etc. provides a complementary binding pair member, or a unique site for further modification, such as chemical cross-linking, biotinylation, etc. that will provide a complementary binding pair member. An alternative strategy is to introduce an unpaired cysteine residue to the subunit, thereby introducing a unique and chemically reactive site for binding. The attachment site may also be a naturally occurring or introduced epitope, where the multivalent binding partner will be an antibody, e.g. IgG, IgM, etc. Any modification will be at a site, e.g. C-terminal proximal, that will not interfere with binding.

Exemplary of multimer formation is the introduction of the recognition sequence for the enzyme BirA, which catalyzes biotinylation of the protein substrate. The monomer with a biotinylated subunit is then bound to a multivalent binding partner, e.g. streptavidin or avidin, to which biotin binds with extremely high affinity. Streptavidin has a valency of 4, providing a multimer of $(\alpha$-$\beta$-P$)_4$.

The multivalent binding partner may be free in solution, or may be attached to an insoluble support. Examples of suitable insoluble supports include beads, e.g. magnetic beads, membranes and microtiter plates. These are typically made of glass, plastic (e.g. polystyrene), polysaccharides, nylon or nitrocellulose. Attachment to an insoluble support is useful when the binding complex is to be used for separation of T cells.

Frequently, the multimeric complex will be labeled, so as to be directly detectable, or will be used in conjunction with secondary labeled immunoreagents which will specifically bind the complex. In general the label will have a light detectable characteristic. Preferred labels are fluorophors, such as fluorescein isothiocyanate (FITC), rhodamine, Texas Red, phycoerythrin and allophycocyanin. Other labels of interest may include dyes, enzymes, chemiluminescers, particles, radioisotopes, or other directly or indirectly detectable agent. Conveniently, the multivalent binding partner will have the labeling group. Alternatively, a second stage label may be used, e.g. labeled antibody directed to one of the peptide constituents, and the like.

The binding complex will be used to detect and/or separate antigen specific T cells. The T cells may be from any source, usually having the same species of origin as the MHC heterodimer. The T cells may be from an in vitro culture, or a physiologic sample. For the most part, the physiologic samples employed will be blood or lymph, but samples may also involve other sources oft cells, particularly where T cells may be invasive. Thus other sites of interest are tissues, or associated fluids, as in the brain, lymph node, neoplasms, spleen, liver, kidney, pancreas, tonsil, thymus, joints, synovia, and the like. The sample may be used as obtained or may be subject to modification, as in the case of dilution, concentration, or the like. Prior treatments may involve removal of cells by various techniques, including centrifugation, using Ficoll-Hypaque, panning, affinity separation, using antibodies specific for one or more markers present as surface membrane proteins on the surface of cells, or any other technique that provides enrichment of the set or subset of cells of interest.

The binding complex is added to a suspension comprising T cells of interest, and incubated at about 4° C. for a period of time sufficient to bind the available cell surface receptor. The incubation will usually be at least about 5 minutes and usually less than about 30 minutes. It is desirable to have a sufficient concentration of labeling reagent in the reaction mixture, so that labeling reaction is not limited by lack of labeling reagent. The appropriate concentration is determined by titration. The medium in which the cells are labeled will be any suitable medium as known in the art. If live cells are desired a medium will be chosen that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

Where a second stage labeling reagent is used, the cell suspension may be washed and resuspended in medium as described above prior to incubation with the second stage reagent. Alternatively, the second stage reagent may be added directly into the reaction mix.

A number of methods for detection and quantitation of labeled cells are known in the art. Flow cytometry is a convenient means of enumerating cells that are a small percent of the total population. Fluorescent microscopy may also be used. Various immunoassays, e.g. ELISA, RIA, etc. may used to quantitate the number of cells present after binding to an insoluble support.

Flow cyometry may also be used for the separation of a labeled subset of T cells from a complex mixture of cells. The cells may be collected in any appropriate medium which maintains the viability of the cells, usually having a cushion of serum at the bottom of the collection tube. Various media are commercially available as described above. The cells may then be used as appropriate.

Alternative means of separation utilize the binding complex bound directly or indirectly to an insoluble support, e.g. column, microtiter plate, magnetic beads, etc. The cell sample is added to the binding complex. The complex may be bound to the support by any convenient means. After incubation, the insoluble support is washed to remove non-bound components. From one to six washes may be employed, with sufficient volume to thoroughly wash non-specifically bound cells present in the sample. The desired cells are then eluted from the binding complex. In particular the use of magnetic particles to separate cell subsets from complex mixtures is described in Miltenyi et al. (1990) Cytometry 11:231-238.

Detecting and/or quantitating specific T cells in a sample or fraction thereof may be accomplished by a variety of specific assays. In general, the assay will measure the binding between a patient sample, usually blood derived, generally in the form of plasma or serum and the subject multimeric binding complexes. The patient sample may be used directly, or diluted as appropriate, usually about 1:10 and usually not more than about 1:10,000. Assays may be performed in any physiological buffer, e.g. PBS, normal saline, HBSS, dPBS, etc.

A sandwich assay is performed by first attaching the multimeric binding complex to an insoluble surface or support. The multimeric binding complex may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently.

The insoluble supports may be any compositions to which the multimeric binding complex can be bound, which is readily separated from soluble material, and which is otherwise compatible with the overall method of measuring T cells. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding patient samples or fractions thereof, the non-specific binding sites on the insoluble support i.e. those not occupied by the multimeric binding complex, are generally blocked. Preferred blocking agents include non-interfering proteins such as bovine serum albumin, casein, gelatin, and the like. Samples, fractions or aliquots thereof are then added to separately assayable supports (for example, separate wells of a microtiter plate) containing support-bound multimeric binding complex.

Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for T cells to bind the insoluble binding complex. Generally, from about 0.1 to 3 hr is sufficient, usually 1 hr sufficing.

After incubation, the insoluble support is generally washed of non-bound components. Generally, a dilute physiologic buffer at an appropriate pH, generally 7–8, is used as a wash medium. From one to six washes may be employed, with sufficient volume to thoroughly wash non-specifically bound T cells present in the sample.

After washing, a solution containing specific second receptor is applied. The receptor may be any compound that binds patient T cells with sufficient specificity such that they can be distinguished from other components present. In a preferred embodiment, second receptors are antibodies specific for common T cell antigens, either monoclonal or polyclonal sera, e.g. anti-thy-1, anti-CD45, etc.

T cell specific antibodies may be labeled to facilitate direct, or indirect quantification of binding. Examples of labels that permit direct measurement include radiolabels, such as $^3H$ or $^{125}I$, fluorescers, dyes, beads, chemilumninescers, colloidal particles, and the like. Examples of labels which permit indirect measurement of binding include enzymes where the substrate may provide for a colored or fluorescent product. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

Alternatively, the second receptor may be unlabeled. In this case, a labeled second receptor-specific compound is employed which binds to the bound second receptor. Such a second receptor-specific compound can be labelled in any of the above manners. It is possible to select such compounds such that multiple compounds bind each molecule of bound second receptor. Examples of second receptor/second receptor-specific molecule pairs include antibody/anti-antibody and avidin (or streptavidin)/biotin. Since the resultant signal is thus amplified, this technique may be advantageous where only a small number oft cells are present. An example is the use of a labeled antibody specific to the second receptor. More specifically, where the second receptor is a rabbit anti-allotypic antibody, an antibody directed against the constant region of rabbit antibodies provides a suitable second receptor specific molecule. The anti-immunoglobulin will usually come from any source other than human, such as ovine, rodentia, particularly mouse, or bovine.

The volume, composition and concentration of T cell specific receptor solution provides for measurable binding to the T cells already bound to the insoluble substrate. Generally, the same volume as that of the sample is used: from about 0.001 to 1 ml is sufficient, usually about 0.1 ml sufficing. When antibody ligands are used, the concentration generally will be about 0.1 to 50 µg/ml, preferably about 1 µg/ml. The solution containing the second receptor is generally buffered in the range of about pH 6.5–9.5. The solution may also contain an innocuous protein as previously described. The incubation time should be sufficient for the labeled ligand to bind available molecules. Generally, from about 0.1 to 3 hr is sufficient, usually 1 hr sufficing.

After the second receptor or second receptor-conjugate has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and is O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490–495 nm is conveniently measured with a spectrophotometer.

Generally the number of bound T cells detected will be compared to control samples from samples having a different MHC context, e.g. T cells from an animal that does not express the MHC molecule used to make the binding complex.

An alternative protocol is to provide anti-T cell reagent, e.g. anti-thy-1, anti-CD45, etc. bound to the insoluble surface. After adding the sample and washing away non-specifically bound T cells, one or a combination of the subject binding complexes are added, where the binding complexes are labeled so as not to interfere with the binding to T cells.

It is particularly convenient in a clinical setting to perform the assays in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it the multimeric binding complex, with a conjugate of an enzyme with T cell specific antibody employed as a reagent, generally added to the sample before application. Alternatively, the binding complex may be conjugated to an enzyme, with T cell specific antibody bound to the measurement region.

Detection of T cells is of interest in connection with a variety of conditions associated with T cell activation. Such conditions include autoimmune diseases, e.g. multiple sclerosis, myasthenia gravis, rheumatoid arthritis, type 1 diabetes, graft vs. host disease, Grave's disease, etc.; various forms of cancer, e.g. carcinomas, melanomas, sarcomas, lymphomas and leukemias. Various infectious diseases such as those caused by viruses, e.g. HIV-1, hepatitis, herpesviruses, enteric viruses, respiratory viruses, rhabdovirus, rubeola, poxvirus, paramyxovirus, morbillivirus, etc. are of interest. Infectious agents of interest also include bacteria, such as Pneumococcus, Staphylococcus, Bacillus. Streptococcus, Meningococcus, Gonococcus, Eschericia, Klebsiella, Proteus, Pseudomonas, Salmonella, Shigella, Hemophilus, Yersinia, Listeria, Corynebacterium, Vibrio, Clostridia, Chlamydia, Mycobacterium, Helicobacter and Treponema; protozoan pathogens, and the like. T cell associated allergic responses may also be monitored, e.g. delayed type hypersensitivity or contact hypersensitivity involving T cells.

Of particular interest are conditions having an association with a specific peptide or MHC haplotype, where the subject binding complexes may be used to track the T cell response with respect to the haplotype and antigen. A large number of associations have been made in disease states that suggest that specific MHC haplotypes, or specific protein antigens are responsible for disease states. However, direct detection of reactive T cells in patient samples has not been possible. Detection and quantitation with the subject binding complexes allows such direct detection. As examples, the activity of cytolytic T cells against HIV infected CD4$^+$ T cells may be determined with the subject methods. The association of diabetes with the DQB1*0302 (DQ3.2) allele may be investigated by the detection and quantitation of T cells that recognize this MHC protein in combination with various peptides of interest. The presence of T cells specific for peptides of myelin basic protein in conjunction with MHC proteins of multiple sclerosis patients may be determined. The antigenic specificity may be determined for the large number of activated T cells that are found in the synovial fluid of rheumatoid arthritis patients. It will be appreciated that the subject methods are applicable to a number of diseases and immune-associated conditions.

The isolation of antigen specific T cells finds a wide variety of applications. The isolated T cells cells may find use in the treatment of cancer as in the case of tumor-infiltrating lymphocytes. Specific T cells may be isolated from a patient, expanded in culture by cytokines, antigen stimulation, etc., and replaced in the autologous host, so as to provide increased immunity against the target antigen. A patient sample may be depleted oft cells reactive with a specific antigen, to lessen an autoimmune response.

The DNA sequence of single T cell receptors having a given antigen specificity is determined by isolating single cells by the subject separation method. Conveniently, flow cytometry may h used to isolate single T cell, in conjunction with single cell PCR amplification. In order to amplify unknown TCR sequences, ligation anchor PCR may be used. One amplification primer is specific for a TCR constant region. The other primer is ligated to the terminus of cDNA synthesized from TCR encoding mRNA. The variable region is amplified by PCR between the constant region sequence and the ligated primer.

Inhibition of immune function may be achieved by inducing anergy of specific T cells, or by ablation of reactive T cells. The subject binding complexes allow a therapy to be targeted to very specific subsets of T cells. The ability to inhibit immune system functions is known to be therapeutically useful in treating a variety of diseases such as atherosclerosis, allergies, autoimmune diseases, certain malignancies, arthritis, inflammatory bowel diseases, transplant rejection and reperfusion injury. Specific diseases of interest include systemic lupus erythematosus; rheumatoid arthritis; polyarteritis nodosa; polymyositis and dermatomyositis progressive systemic sclerosis (diffuse scleroderma); glomerulonephritis; myasthenia gravis; Sjogren's syndrome; Hashimoto's disease; Graves' disease; adrenalitis; hypoparathyroidism; pernicious anemia; diabetes; multiple sclerosis, and related demyelinating diseases; uveitis; pemphigus and pemphigoid cirrhosis; ulcerative colitis; myocarditis; regional enteritis; adult respiratory distress syndrome; local manifestations of drug reactions, such as dermatitis, etc.; inflammation-associated or allergic reaction patterns of the skin; atopic dermatitis and infantile eczema; contact dermatitis; psoriasis; lichen planus; allergic enteropathies; allergic rhinitis; bronchial asthma; transplant rejection, e.g. heart, kidney, lung, liver, pancreatic islet cell, etc.; hypersensitivity or destructive responses to infectious agents; poststreptococcal diseases, e.g. cardiac manifestations of rheumatic fever, and the like.

To ablate specific T cells, the subject binding complexes may be conjugated to a toxin moiety. Various cytotoxic agents are known and have been used in conjunction with specific binding molecules. Illustrative of these compounds are ricin, abrin, diphtheria toxin, maytansinoids, cisplatin, and the like. Where there are two subunits, only the cytotoxic subunit may be used, e.g. the α-unit of ricin. The toxin is conjugated to the binding complex, generally by means of a cross-linker, or other conjugation that includes a disulfide bond. Toxin conjugates are disclosed in U.S. Pat. Nos. 5,208,020; 4,863,726; 4,916,213; and 5,165,923. The toxin conjugate is administered so as to specifically eliminate the target T cells without exerting significant toxicity against other cells.

The subject binding complexes may be administered to a host to induce anergy of the specific T cells. The binding complex will induce T cell anergy upon binding, because the co-stimulator molecules necessary for T cell activation are not present. The binding complexes are administered to individuals, preferably mammals, in a manner that will maximize the likelihood of the binding complexes reaching the targeted T cell and binding to it, and thereby inducing anergy. This in turn will inhibit the immune response mediated by that T cell.

The dose for individuals of different species and for different diseases is determined by measuring the effect of the binding complexes on the lessening of these parameters which are indicative of the disease being treated. The binding complexes will normally be administered parenterally, preferably intravenously. Doses of binding complexes in a mouse model will generally range from about 0.5–2 mg/host/week for from about 1 to 4 weeks. The dose of the binding complexes may have to be repeated periodically depending upon the particular disease.

When administered parenterally, the binding complexes will be formulated in an injectable dosage form (solution, suspension, emulsion) in association with a pharmaceutically acceptable parenteral vehicle. Such vehicles are inherently non-toxic and non-therapeutic. Examples of such vehicles are water, saline, Ringer's solution, dextrose solution, and Hanks' solution. Non-aqueous vehicles such as fixed oils and ethyl oleate may also be used. The vehicle may contain minor amounts of additives, such as substances that enhance isotonicity and chemical stability, e.g. buffers and preservatives. The binding complexes are preferably formulated in purified form substantially free of aggregates and other proteins at concentrations of about 1–50 mg/ml. Suitable pharmaceutical vehicles and their formulations are described in Remington's Pharmaceutical Sciences, by E. W. Martin, which is incorporated herein by reference.

The following examples are offered by way of illustration and not by way of limitation.

EXPERIMENTAL

Synthesis of a Tetrameric MHC Antigen-Peptide Complex

Production of a tetrameric MHC protein-peptide binding complex reagent is performed as follows. Briefly, plasmid vectors were constructed to express a fusion protein of a BirA substrate peptide (BSP) (see Shatz et al. [1993]) joined to one of the chains of a class II MHC molecule. The α chain of the murine I-E$^k$ protein was used.

The fusion protein, termed Ec-I-E$_\alpha^k$-BSP, was expressed in $E.\ coli$. The fusion protein was then folded in vitro with Ec-I-E$_\beta^k$ and the αβ heterodimers purified on an immunoaffinity column (described in Altman et al. [1993] supra. and Wettstein et al. [1991] $J.\ Exp.\ Med.$ 714:219–228). The heterodimers were biotinylated in vitro with purified BirA enzyme. Specific antigenic peptides are then inserted into the MHC heterodimer. The complex is bound to streptavidin previously labeled with Texas Red, and purified by gel filtration chromatography.

Construction of the plasmid for expression of Ec-I-E$_\alpha^k$-BSP.

Using the polymerase chain reaction, DNA coding for the 15 residue BirA substrate peptide (BSP) (SEQ ID NO:1) LHHILDAQKMVWNHR, was fused (Schatz, 1993) to the 3' end of a previously described gene for the expression of soluble I-E$_\alpha^k$ in *E. coli* (Altman, 1993). An antisense oligonucleotide was designed (SEQ ID NO:2) 5'CCGGAAT-TCTTAACGATGATTCCACACCATTTTCT-GTGCATCCAGAATATGATGCAGGAGGAGGGTTTTC-TCTTC3'. In the sense direction the oligonucleotide provides for the 18 bases corresponding to the C-terminus of soluble Ec-I-E$_\alpha^k$, 45 bases encoding the BSP, a stop codon and an EcoR I restriction site, plus flanking bases. The sense primer for the PCR, (SEQ ID NO:3) CATATGGCTAGCAT-CAAAGAGGAACACACCAT has been previously described (Altman, 1993).

The gene coding for the Ec-I-E$_\alpha^k$-BSP fusion was amplified using the Ultma enzyme (Perkin-Elmer/Cetus) according to instructions from the manufacturer, with the supplied buffer components. The amplification mixes contained 50 μM of each dNTP, 1.5 mM MgCl$_2$ and 0.1 μg of the pGEM-EAK plasmid as target DNA. The reaction mixes were subjected to three cycles of 94° C. for 1 min, 45° C. for 1 min, and 72° C. for 1 min. The annealing temperature was then increased from 45° C. to 55° C. for 12 additional cycles, followed by a final incubation at 72° C. for 7 minutes.

The PCR product was digested with NheI and EcoRI and was ligated into the pGEMEX-1 plasmid (Promega) digested with the same enzymes. The plasmids were transformed into the *E. coli* strain JM 109 and clones containing the correct sequence were identified by sequencing of double strand plasmid DNA with Sequenase (Amersham/USB). A plasmid containing the correct sequence for the Ec-I-E$_\alpha^k$-BSP gene was used to transform the BL21(DE3) pLysS strain of *E. coli* for expression of the fusion protein. Expression of Ec-I-E$_\alpha^k$-BSP and in vitro folding Inclusion bodies containing the Ec-I-E$_\alpha^k$-BSP protein were produced following established protocols (Altman et al. [1993]), with the following modifications. Following expression, the protein was solubilized in a buffer lacking reducing agents (e.g. dithiothreitol or mercaptoethanol) but containing all previously described components (6M guanidinium hydrochloride, 50 mM Tris, pH 8.0, 1 mM EDTA). The protein concentration was kept at or below 1 mg/ml, and disulfides were allowed to form by air oxidation over 3–5 days while the protein was still in denaturant. This modified protocol was also followed for the Ec-I-E$_\beta^k$ chain.

Soluble Ec-I-E$^k$ heterodimers were produced in large scale in vitro folding reactions as described (Altman, 1993), except that glutathione and peptide ligands were not included in the folding reactions. Empty Ec-I-E$_k$ α-BSP/β heterodimers were isolated by immunoaffinity chromatography on a column containing the anti-I-E$^k$ monoclonal antibody 14-4-4S as described (Wettstein, 1991). Column elation buffer was exchanged for PBS by diafiltration in Centricon 30 ultrafiltration devices (Amicon).

Enzymatic biotinylation of Ec-I-E$^k$-BSP.

The plasmid pJS169 is a pACYC184 derivative that directs overexpression of BirA under the control of the tac promoter. Following expression and bacterial cell lysis, the BirA protein was purified by column chromatography, first on Fast Flow Blue Sepharose, and then by ion exchange chromatography on a MonoS column (Pharmacia). Each batch of BirA is titered for activity in a reaction mix containing 20 mM Tris (pH 7.5), 5 mM MgCl$_2$, 5 mM ATP, 100 μM biotin, and 2.3 μM Ec-I-E$^k$-BSP. Reactions are incubated for 16 hours at 37° C. Following removal of free biotin by diafiltration on Centricon 30 concentrators, the biotinylation level is assessed by a combination of precipitation with streptavidin-agarose (Sigma) and quantitation of non-precipitible I-E$^k$ by sandwich ELISA. Several dilutions of biotinylated Ec-I-E$^k$-BSP are incubated with a small volume of streptavidin-agarose beads overnight at 4° C. in a buffer containing 2% BSA and 5 mM sodium azide in PBS. Supernatants from these mixes, as well as from control mixes containing unmodified agarose beads, are then assayed by ELISA.

For the ELISA, Immulon-4 plates are coated overnight at 4° C. with 14-4-4S at a concentration of 3.3 μg/ml in PBS. The plates are blocked with 2% BSA in PBS buffer for 1 hour at room temperature. Serial dilutions of solutions containing Ec-I-E$^k$-BSP, as well as a standard containing a known concentration of Ec-1-E$^k$, are incubated on the plate for 1–2 hours at room temperature. After washing of the plate with wash buffer (0.25% BSA/0.05% Tween20/5 mM sodium azide), a rabbit anti-I-E$^k$ antisera was applied at a dilution of 1:4000 to 1:10,000 for 1 hour. Finally, the assay was developed by addition of a mouse absorbed, goat-anti-rabbit-alkaline phosphatase conjugate (incubation time 1 hour) and addition of substrate (Sigma AP 104 tablets). Typically, 90–100% of the I-E$^k$ is removed from the solutions by precipitation with streptavidin-agarose, reflecting nearly complete biotinylation of the Ec-I-E$^k$-BSP protein. Ec-I-E$^k$ proteins lacking the BSP are not biotinylated by this protocol, strongly suggesting biotinylation at a single site in the BSP.

Loading of the bio-Ec-I-E$^k$-BSP with peptide

Enzymatically biotinylated proteins are loaded with the 88–103 peptide from moth cytochrome C, SEQ ID NO:4, ANERADLIAYLKQATK according to established protocols (Wettstein [1991], supra; Reay [1992] supra). The empty αβ heterodimer was incubated with McIlvaine's citric acid-phosphate buffer (CPB) at 37° C. in presilanized microfuge tubes. Reactions were adjected to pH 7 by addition of 2M Na$_2$HPO$_4$. Peptide loaded bio-Ec-I-E$^k$-BSP molecules are purified by gel filtration on Superdex 200 columns, in a PBS mobile phase.

Production of bio-Ec-I-E$^k$-BSP tetramers

Tetramers were produced by mixing the bio-Ec-I-E$^k$-BSP molecules with streptavidin-Texas Red (Boehringer Mannheim) at a 4:1 molar ratio. To maximize production of tetramers, the desired quantity of streptavidin is added in 10 equal steps, with an incubation time of 15 minutes between additions. This ensures that nearly all of the streptavidin added at each addition is saturated with bio-Ec-I-E$^k$-BSP, and after the tenth addition, the reaction mixture contains predominantly bio-Ec-I-E$^k$-BSP tetramers, and small amounts of excess streptavidin and any Ec-I-E$^k$-BSP protein that was not biotinylated by BirA.

The streptavidin-TR binding reactions are first concentrated in Centricon 30 devices, and the minor contaminants are easily removed by gel filtration on Superadex 200 columns. The tetramer elutes from the column in an early peak, corresponding to a molecular weight of approximately 250,000, while the contaminants have molecular weights near 50,000. The labeled tetramers are concentrated to a concentration of 3–4 mg/ml and are stored in PBS+5 mM sodium azide at 4° C. in amber vials prior to use.

Figure 1A:
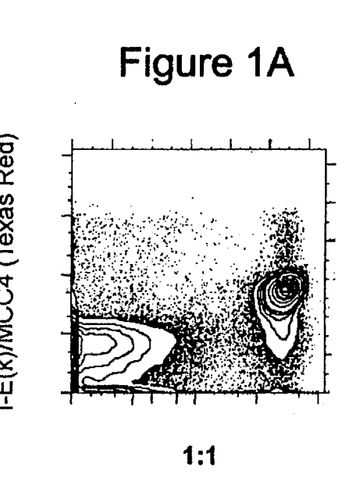
FIGS. 1A to 1D depict FACS analysis of streptavidin(TR) .Ec-I-Ek/MCC)4 selective staining of 5C.C7 tg T cells in mixing experiments.
Figure 1B:
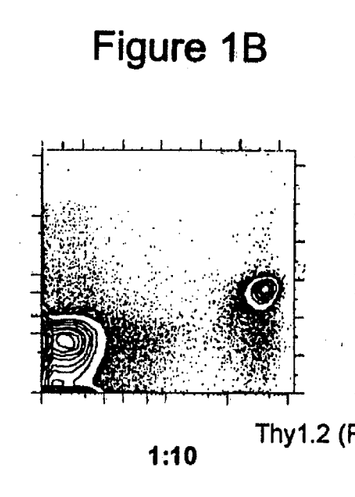
Figure 1C:
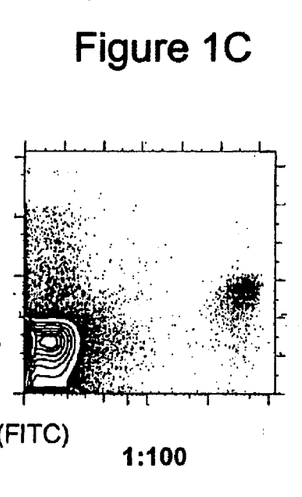
Figure 1D:
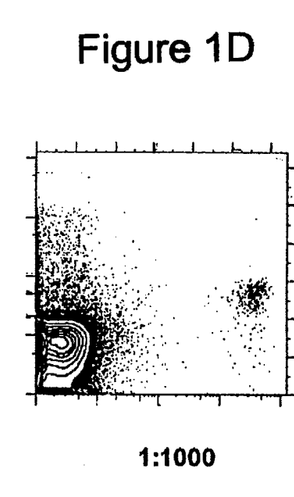

Labeling of Antigen-Specific T cells with a Tetrameric MHC Antigen-Peptide Complex Cells from the draining lymph nodes of a 5C.C7 T cell receptor (TCR) transgenic mouse are mixed with lymph node cells from a non-transgenic AKR/J mouse at varying ratios. The transgenic mouse is described in Seder et al. (1992) *J. Exp. Med.* 1091–1098. It is transgenic for the α and β chain of the 5C.C7 T cell receptor. The 5C.C7 mouse has a B10.BR genetic background, which is I-E$^k$ and Thy 1.2 positive, while the AKR/J strain is also I-E$^k$ positive, but is Thy 1.2 negative. The Thy 1 allotypic marker therefore allows easy identification of T cells from the transgenic mouse. FACS plots display cells which are gated to be CD4+ and negative for CD8, B220, and Mac-1 using the Desk software at the Stanford FAGS facility, data shown in FIG. 1.

The antibodies and concentrations used the staining experiments are listed in Table 1.

TABLE 1

| Antigen | Staining Reagent | Label | Supplier | Final Concentration |
| --- | --- | --- | --- | --- |
| CD4 | YT5 191.1 | APC | Caltag | 10 µg/ml |
| CD8 | 53-6.7 | PE | Pharmingen | 10 µg/ml |
| B220 | RA3-6B2 | PE | Pharmingen | 10 µg/ml |
| Mac-1 | M1/70 | PE | Pharmingen | 10 µg/ml |
| Thy 1.2 | 53-2.1 | FITC | Pharmingen | 10 µg/ml |
|  | Streptavidin | Texas Red | Boehringer-Mannheim | 10 µg/ml |
| TCR | Binding complex | Texas Red | — | 70 µg/ml |

Figure 2A:
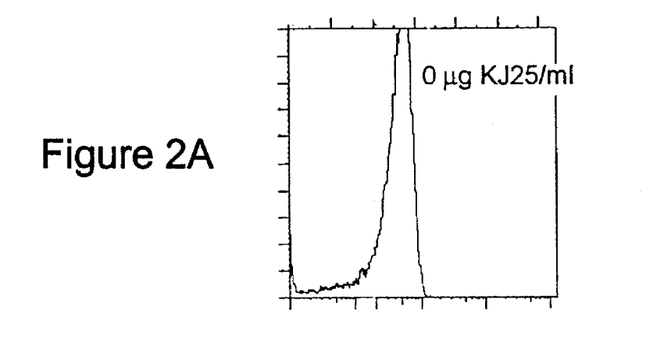
FIGS. 2A to 2D show preblocking with Kj25 prevents binding of SA-TR(bioEc-I-Ek.MCC)4.
Figure 2B:
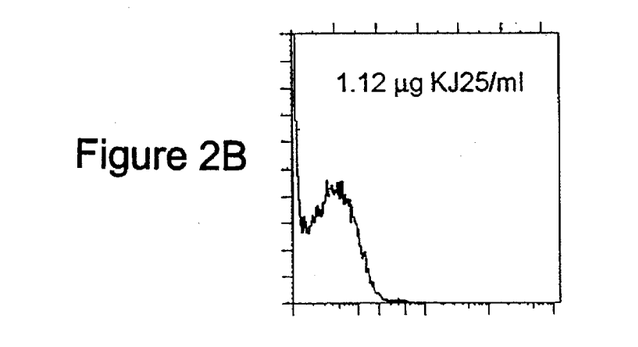
Figure 2C:
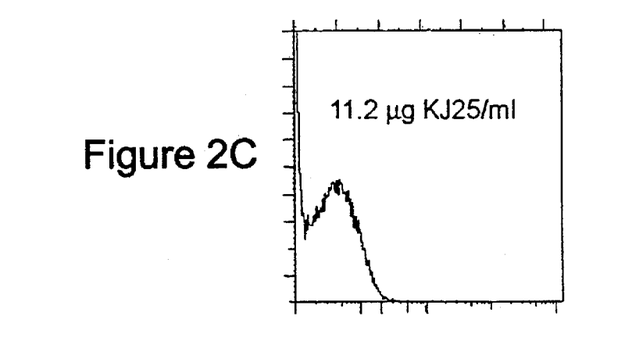
Figure 2D:
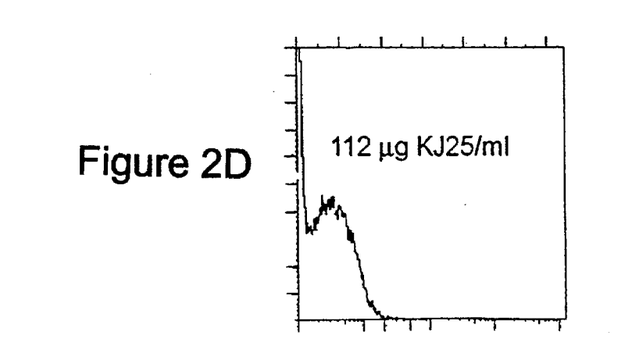

$2\times10^6$ cells, at a concentration of $4\times10^7$ cells/ml were incubated with the staining reagent for 30–60 minutes at 4° C. The cells were washed once with PBS+2% FCS prior to analysis. The data shown in FIG. 1 results from the analysis of $5\times10^5$ cells. The data in FIG. 2 was obtained from analysis of $5\times10^4$ cells.

The mixing experiment demonstrates that the multimeric labeling reagent will bind to the transgenic cells, even in a large background of non-transgenic cells, many of which also recognize peptides bound to I-E$^k$.

The staining with the subject labeling reagent was shown to be specific for the transgenic T cell receptor by the following experiment. 5C.C7 transgenic lymph node cells were preblocked with KJ25 monoclonal antibody, which is specific for the TCR V$_\beta$3 variable regions (The 5C.C7 TCR transgene is V$_\beta$3/V$_\alpha$11). These cells were then stained with the subject labeling reagent. The data is shown in FIG. 2. The displayed cells were gated to be positive for CD4 and negative for B220, CD8 and Mac-1. The KJ25 antibody completely blocked binding of the MHC reagent at the higher concentration.

It is evident from the above results that the subject invention provides for a novel method of specifically labeling T cells according to their antigen receptor. Stable multimeric complexes of MHC proteins and specific antigenic peptides are able to bind to T cells recognizing the complex, allowing the labeling, analysis and separation of the particular T cell subset. The invention allows for the tracking and separation of specific T cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting mammalian T cells according to the specificity of their antigen receptor, the method comprising:

combining a suspension of said T cells and a multimeric binding complex having the formula:

(α-β-P)$_n$, wherein α-β-P is an MHC peptide complex monomer

α comprises a soluble form of an α chain of a class I or class II MHC protein,

β comprises a soluble form of (i) a β chain of a class II MHC protein or (ii) β$_2$ microglobulin for a class I MHC protein; and P comprises a substantially homogeneous peptide antigen bound in the groove formed by two membrane distal domains of (i) said α chain for a class I MHC protein or (ii) said α chain and said β chains for a class II MHC protein;

wherein n is greater than or equal to 2, and said multimeric binding complex is formed by binding said monomer to a multivalent entity through specific attachment sites on said α or said β chain;

detecting the presence of specific binding of said multimeric binding complex and said T cells;

wherein said complex is bound to T cells comprising an antigen receptor specific for said peptide antigen presented by said α and said β MHC chains.

2. A method according to claim 1, wherein n equals 4.

3. A method according to claim 1, wherein at least one of said α and said β chains is derived from a fusion protein comprising an amino acid recognition sequence for a modifying enzyme selected from the group consisting of BirA, glycosylase, farnesyl protein transferase and protein kinase.

4. A method according to claim 3, wherein said modifying enzyme is BirA, said fusion protein is biotinylated, and said multivalent entity comprises at least one of streptavidin and avidin.

5. A method according to claim 4, wherein said multimeric binding complex further comprises a detectable label.

6. A method for separation of mammalian T cells according to their antigen receptor, the method comprising:

combining a suspension of said T cells and a multimeric binding complex having the formula:

(α-β-P)$_n$, wherein α-β-P is an MHC peptide complex monomer,

α comprises a soluble form of an α chain of a class I or class II MHC protein,

β comprises a soluble form of (i) a β chain of a class II MHC protein or (ii) β$_2$ microglobulin for a class I MHC protein; and P comprises a substantially homogeneous peptide antigen bound in the groove formed by two membrane by distal domains of (i) said α chain for a class I MHC protein or (ii) said α chain and said β chains for a class II MHC protein;

wherein n is greater than or equal to 2, and said multimeric binding complex is formed by binding said monomer to a multivalent entity through specific attachment sites on said α or said β chain;

separating cells bound to said complex from unbound cells;

wherein said complex is bound to T cells comprising an antigen receptor specific for said peptide antigen presented by said α and said β MHC chains.

7. A method according to claim 6, wherein n equals 4.

8. A method according to claim 6, wherein at least one of said α and said β chains is derived from a fusion protein comprising an amino acid recognition sequence for a modifying enzyme selected from the group consisting of BirA, glycosylase, farnesyl protein transferase and protein kinase.

9. A method according to claim 8, wherein said modifying enzyme is BirA, said fusion protein is biotinylated, and said multivalent entity comprises at least one of streptavidin and avidin.

10. A method according to claim 9, wherein said multimeric binding complex further comprises a light detectable label.

11. A method according to claim 10, wherein said separating is by flow cytometry.

12. A multimeric binding complex for labeling mammalian T cells according to their antigen receptor, having the formula:

$(\alpha\text{-}\beta\text{-}P)_n$, wherein $\alpha\text{-}\beta\text{-}P$ is an MHC peptide complex monomer, $\alpha$ comprises a soluble form of an $\alpha$ chain of a class I or class II MHC protein, $\beta$ comprises a soluble form of (i) a $\beta$ chain of a class II MHC protein or (ii) β2 microglobulin for a class I MHC protein; and P comprises a substantially homogeneous peptide antigen bound in the groove formed by two membrane distal domains of (i) said $\alpha$ chain for a class I MHC protein or (ii) said $\alpha$ chain and said $\beta$ chains for a class II MHC protein;

wherein n is greater than or equal to 2, and said multimeric binding complex is formed by binding said monomer to a multivalent entity through specific attachment sites on said $\alpha$ said $\beta$ chain.

13. A multimeric binding complex according to claim 12, wherein n equals 4.

14. A multimeric binding complex according to claim 12, wherein at least one of said $\alpha$ and said $\beta$ chains is derived from a fusion protein comprising an amino acid recognition sequence for a modifying enzyme selected from the group consisting of BirA, glycosylase, farnesyl protein transferase and protein kinase.

15. A multimeric binding complex according to claim 14, wherein said modifying enzyme is BirA, said fusion protein is biotinylated, and said multivalent entity comprises at least one of streptavidin and avidin.

16. A binding complex according to claim 15, wherein said multimeric binding complex further comprises a light detectable label.

* * * * *